US010431008B2

(12) United States Patent
Djajadiningrat et al.

(10) Patent No.: US 10,431,008 B2
(45) Date of Patent: Oct. 1, 2019

(54) REMOTE ASSISTANCE WORKSTATION, METHOD AND SYSTEM WITH A USER INTERFACE FOR REMOTE ASSISTANCE WITH SPATIAL PLACEMENT TASKS VIA AUGMENTED REALITY GLASSES

(71) Applicant: KONINKLIJKE PHILIPS N.V., Eindhoven (NL)

(72) Inventors: Johan Partomo Djajadiningrat, Utrecht (NL); Pei-Yin Chao, Eindhoven (NL); Wing Lam Lui, The Hague (NL)

(73) Assignee: KONINKLIJKE PHILIPS N.V., Eindhoven (NL)

(*) Notice: Subject to any disclaimer, the term of this patent is extended or adjusted under 35 U.S.C. 154(b) by 0 days.

(21) Appl. No.: 15/772,287

(22) PCT Filed: Oct. 12, 2016

(86) PCT No.: PCT/IB2016/056084
§ 371 (c)(1),
(2) Date: Apr. 30, 2018

(87) PCT Pub. No.: WO2017/072616
PCT Pub. Date: May 4, 2017

(65) Prior Publication Data
US 2018/0322702 A1 Nov. 8, 2018

Related U.S. Application Data

(60) Provisional application No. 62/247,797, filed on Oct. 29, 2015.

(51) Int. Cl.
G06T 19/00 (2011.01)
G06F 19/00 (2018.01)
(Continued)

(52) U.S. Cl.
CPC .......... *G06T 19/006* (2013.01); *A61B 5/0404* (2013.01); *A61B 90/36* (2016.02);
(Continued)

(58) Field of Classification Search
None
See application file for complete search history.

(56) References Cited

U.S. PATENT DOCUMENTS

2013/0237811 A1   9/2013  Mihailescu et al.
2014/0354528 A1  12/2014  Laughlin et al.

FOREIGN PATENT DOCUMENTS

WO   2012164155 A1   12/2012
WO   2014076236 A1    5/2014
WO   2014100688 A2    6/2014

OTHER PUBLICATIONS

Bottecchia et al: "A New AR Interaction Paradigm for Collaborative Teleassistance System: The POA"; Int J Interact Des Manuf (2009) 3:35-40.

(Continued)

Primary Examiner — Vu Nguyen

(57) ABSTRACT

A remote assistance workstation 12 comprises a communications module 54, a user interface (UI) module 52, and a controller 56, for being coupled to a portable device 14 that includes a pair of augmented reality (AR) glasses 36 worn by a first responder to carry out an action using an object with a subject at a scene. The UI module 52 renders a remote assistant graphical user interface (GUI) 100 that includes (i) a first pane 96 for displaying a live video stream of a remote assistance request and (ii) a second pane 98 for displaying a 2D representation of the object at the scene being moveable therein by remote assistant inputs. The GUI 100 renders a corresponding item of 3D virtual content within the first pane relative to a reference point. The controller 56 outputs remote assistance signals to the portable device 14 for (Continued)

displaying the item of 3D virtual content 38 on the AR glasses in a live view of the scene, appearing at a location determined by the remote assistant inputs moving the 2D representation within the second pane 98 for assisting the first responder at the scene.

20 Claims, 8 Drawing Sheets

(51) Int. Cl.
| | |
|---|---|
| *G16H 80/00* | (2018.01) |
| *A61B 90/00* | (2016.01) |
| *G16H 40/67* | (2018.01) |
| *G06F 9/451* | (2018.01) |
| *A61B 5/0404* | (2006.01) |
| *A61H 31/00* | (2006.01) |
| *A61N 1/39* | (2006.01) |
| *G02B 27/01* | (2006.01) |
| *A61B 90/50* | (2016.01) |
| *A62B 99/00* | (2009.01) |
| *G06F 3/041* | (2006.01) |
| *G06K 9/00* | (2006.01) |
| *G06T 3/20* | (2006.01) |
| *G06T 3/60* | (2006.01) |

(52) U.S. Cl.
CPC ......... *A61H 31/007* (2013.01); *A61N 1/3993* (2013.01); *G02B 27/0172* (2013.01); *G06F 9/453* (2018.02); *G06F 19/3418* (2013.01); *G06F 19/3481* (2013.01); *G16H 40/67* (2018.01); *G16H 80/00* (2018.01); *A61B 2090/365* (2016.02); *A61B 2090/502* (2016.02); *A62B 99/00* (2013.01); *G02B 2027/0134* (2013.01); *G02B 2027/0138* (2013.01); *G02B 2027/0141* (2013.01); *G02B 2027/0178* (2013.01); *G06F 3/041* (2013.01); *G06K 9/00221* (2013.01); *G06T 3/20* (2013.01); *G06T 3/60* (2013.01); *G06T 2200/24* (2013.01)

(56) References Cited

OTHER PUBLICATIONS

Gauglitz et al: "Integrating the Physical Environment Into Mobile Remote Collaboration"; Mobilehci'12, Sep. 21-24, 2012 San Francisco, CA, pp. 241-250.

REMOTE ASSISTANCE WORKSTATION, METHOD AND SYSTEM WITH A USER INTERFACE FOR REMOTE ASSISTANCE WITH SPATIAL PLACEMENT TASKS VIA AUGMENTED REALITY GLASSES

CROSS-REFERENCE TO PRIOR APPLICATIONS

This application is the U.S. National Phase application under 35 U.S.C. § 371 of International Application No. PCT/IB2016/056084, filed on Oct. 12, 2016, which claims the benefit of U.S. Provisional Patent Application No. 62/247,797, filed on Oct. 29, 2015. These applications are hereby incorporated by reference herein.

The present embodiments relate generally to the providing of remote assistance and more particularly, to a remote assistance workstation, method and system with a user interface for providing remote assistance with spatial placement tasks via augmented reality glasses.

Various methods and systems are known in the art in which a remote assistant or expert uses some form of video collaboration or other remote assistance tool to provide guidance to a person in need of assistance. One known method includes interacting with augmented reality displays, such as augmented reality glasses, and is facilitated via receiving a visual recording of a field of view from a first user's augmented reality device and displaying it on a remote assistant's display device. The method further includes receiving an indication of a touch input to the remote assistant's display device and determining, by a processor, a location of the input within the image and causing information regarding the location of the input to be provided to the augmented reality device such that an indication (i.e., an arrow icon) may be imposed upon the view provided by the augmented reality at the location of the input. However, the providing of an arrow icon by such methods and systems is highly inadequate under certain circumstances, for example, in the case of medical emergency situations.

In other words, an arrow icon on a display is of limited use, especially for emergency situations in which a first responder needs more than simple two-dimensional (2D) assistance, but rather three-dimensional (3D) guidance. For example, to deliver high quality CPR, not only does the first responder need to position his or her hands in the proper location on a victim's chest, but the first responder also needs to act with the right depth (i.e., compression of the victim's chest) and speed (i.e., frequency of compression). Guidelines recommend a depth of two inches (2 in). Compressions move blood through the body to keep vital organs oxygenated. In addition, adequate depth essentially traps the heart between the sternum and spine and effectively squeezes the blood out. Otherwise, inadequate CPR occurs.

Furthermore, in an emergency situation, a first responder may be using a currently known CPR metronome which guides the first responder in deploying a same compression depth for thin as well as large people. A problem exists in that deploying too little depth is ineffective and deploying too much depth potentially leads to damage to structures being compressed, for example, especially with respect to CPR chest compression depth in children. Also, rib fracture is known to happen during CPR, which in turn causes other complications. Another problem in administering CPR is incomplete chest release. While the depth of compression, i.e., compressing the chest deep enough, is important, it is also important to release the pressure on the victim's chest sufficiently. If the first responder does not raise his hands sufficiently, the victim's chest remains compressed and the pumping effect on the heart is diminished.

In addition to CPR for emergency care, automatic external defibrillators (AEDs) are also known. With the use of an AED, resuscitation must be done according to a strict and time critical protocol. Typically, resuscitation of a victim is started by an informal caregiver (e.g., a colleague, a family member, a bystander) since the first minutes of the emergency are crucial and it will take time for someone to arrive with an AED. For resuscitation (i.e. pumping action on the victim's chest, alternated with mouth-to-mouth) to function correctly, the informal caregiver needs to act with the right depth (i.e., compression of the victim's chest) and speed (i.e., frequency of compression).

Further in connection with defibrillation and emergency care with an AED, it is noted that when a heart is fibrillating, disorganized electrical signals disrupt the synchronized contraction of the heart muscles. The AED device can help to bring the heart's electrical signals back in sync by administering an electric shock. To administer this shock, two adhesive electrode pads need to be positioned onto the victim's body in certain locations and orientations. In particular, the electrode pads need to be put along a body diagonal with the heart located in between the electrode pads. An optimal placement for an adult patient involves the first pad being attached to the upper right chest, and then the second pad being attached to the lower left side of the victim. For a professional caregiver this may be easy, but for an informal caregiver this can be tricky. Some AEDs may provide a step-by-step verbal instruction and/or illustrations that assist an informal caregiver to correctly use the electrode pads and the device. However, for a lay person guided only by an illustration on the electrode pads themselves, it may be difficult to put the pads in an optimal location on a victim needing emergency care.

In addition to the problems discussed above with respect to administering CPR, another problem in using an AED is incorrect electrode pad placement on a victim. For optimal defibrillation, the two electrode pads should be placed correctly on the victim's body. Medical professionals generally know how to place the pads relative to body features such as nipples, belly button and rib lines. However, a layman first responder typically does not know this information and it is difficult for a product to quickly communicate this complex medical information in an emergency situation with non-dynamic 2D graphics. The non-dynamic 2D graphics are usually found illustrated on each AED electrode pad are difficult to relate to the victim's body.

Every second counts during cardiac arrest. Accordingly, it would be desirable to provide a remote assistance workstation, method and system with a graphical user interface for providing remote assistance to a first responder with spatial placement tasks via augmented reality glasses, e.g., for cutting down on the time needed to start resuscitation or other emergency treatment, and thus improving the chances of survival for a victim. Accordingly, an improved method and apparatus for overcoming the problems in the art is desired.

In accordance with one aspect of the present disclosure, with the advent of augmented reality headsets, it becomes possible for "a person present at a scene" wearing such augmented reality headsets or glasses to connect to a remote expert. The remote expert can then see a live stream captured by the camera in the AR glasses and "see through the eyes" of the "person present at the scene." Possible use cases are a first responder in an emergency situation being assisted by a medical expert in a 911 call centre and a field technician or engineer carrying out maintenance or repair consulting a remote expert in a back-office who is more knowledgeable on a particular machine, certain procedures, availability of components, etc. The first use case is highly relevant to emergency care, most notably a product-service combination in which an emergency response team can remotely support first responders. The second use case is highly relevant, for example in the healthcare business, in which maintenance engineers in the field have to carry out work on specialized medical equipment (e.g. MRI, CT, iXR and ultrasound scanners, patient monitors etc.). The second use case is also relevant in the lighting business with respect to lighting systems (e.g. office lighting, street lighting, etc.). Essential to this type of application is how the remote expert, using a graphical user interface according to the present embodiments, can provide virtual 2D and 3D graphical guidance in the AR glasses worn by the person at the scene.

According to one embodiment of the present disclosure, a graphical user interface for use by a remote expert in providing remote assistance via augmented reality glasses comprises at least two panes. A first pane includes a live video stream view obtained from a camera in the augmented reality glasses. A second pane includes a representation illustrating a 2D view of a given orientation (e.g., a top view or other orientation) of the remote scene and various moveable 2D representations of 3D virtual objects relevant to the remote assistance being rendered, and more particularly, illustrating a 2D view of virtual content which can be selected and moved relative to a reference point in the 3D scene. The virtual objects are selectable and moveable, via the expert assistant inputs, within at least the second pane.

The remote assistant graphical user interface GUI offers the remote expert at least two modes for communicating information to the "person present at the scene." In a first mode, the remote expert can highlight any part in the live video stream in the first pane through selecting, e.g., via touching a touch screen display having the live video stream in the first pane displayed thereon, an (x,y) coordinate and exactly the same part will be highlighted in the stereoscopic AR glasses for the person wearing the AR glasses to see. The virtual highlight is stationary with respect to the frame of the live view pane (i.e., for the expert) as well as with respect to the AR glasses. Therefore this first mode only works if the person at the scene holds his or her head still temporarily, as otherwise the view on the scene will 'slide' relative to the virtual highlight. In a second mode, the remote expert can select and move (i.e., drag) virtual content around in the 2D representation of the scene as displayed in the second pane. Because the virtual content, as moved in the second pane of the user interface by the remote assistant, is positioned relative to a fixed reference point in the 3D scene, it does not matter if the person wearing the AR glasses moves his or her head: the remote expert can move the virtual content without the virtual content jumping about with the movements of the augmented reality glasses.

Most importantly, the remote assistant cannot simply move content within the first pane (i.e., the live video stream) as the first responder is moving his or her head. The latter situation makes it impossible for the remote expert to keep the 3D virtual content steady, i.e., within the live video stream of the first pane. Accordingly, the remote assistance workstation utilizes an indirect application of the 3D virtual content via the second pane (i.e., the 2D top view or other desired 2D orientation view). The remote assistant selects and moves 2D representations of the 3D virtual content within the 2D top view of the subject or second object at the scene. Subsequent to placement of the 3D virtual content in a desired location within the 2D top view by the remote assistant, the controller of the remote assistance workstation produces remote assistance signals for causing the 3D virtual content to be displayed within the live video stream and held steady with respect to a reference point in the live video stream.

According to one embodiment, a remote assistance workstation is configured for being operatively coupled to a portable device that comprises at least a pair of stereoscopic augmented reality glasses, the portable device for use by a first responder to carry out at least one action using a first object at a scene in connection with at least one of a subject and a second object at the scene. The remote assistance workstation comprises a communications module, a user interface module, and a controller. The communications module is configured for communicating with the portable device in response to a remote assistance request initiated from the portable device; the remote assistance request including at least a live video stream captured via a camera of the stereoscopic augmented reality glasses at the scene.

The user interface module is configured for (a) rendering a remote assistant graphical user interface on a display device and (b) receiving remote assistant inputs from a remote assistant. The remote assistant graphical user interface includes at least (i) a first pane for displaying the live video stream of the remote assistance request, and (ii) a second pane for displaying a 2D representation of the first object at the scene. The rendered 2D representation is moveable within the second pane in response to one or more remote assistant inputs. The remote assistant graphical user interface is further configured for rendering within the first pane a corresponding at least one item of 3D virtual content, corresponding to the 2D representation of the first object at the scene, relative to at least a reference point within the first pane. The reference point is based upon a content of the live video stream.

The controller is configured for generating one or more remote assistance signals to be output, via the communications module, to the portable device for displaying the at least one item of 3D virtual content on the stereoscopic augmented reality glasses to the first responder within a live view of the scene as is captured by the camera of the AR glasses. The at least one item of 3D virtual content appears at a correct location with respect to the reference point within the live view in response to the one or more remote assistant inputs moving the 2D representation of the first object at the scene within the second pane of the remote assistant graphical user interface, for assisting the first responder to carry out the at least one action using the first object in connection with the subject or the second object at the scene.

In another embodiment, the portable device comprises a portable medical device that includes at least one of an automated external defibrillator (AED), a cardiopulmonary resuscitation (CPR) metronome, and an electrocardiogram (ECG) monitor. In addition, the first object at the scene comprises one or more of (i) a first responder's hand, hands, or other first responder body part, and (ii) at least one item of the portable device.

In a further embodiment, the at least one item of 3D virtual content comprises at least one virtual representation outline that is representative of at least one of (i) the first responder's hand, hands, or other first responder body part, and (ii) the at least one item of the portable device.

According to another embodiment, the remote assistance workstation further comprises one or more of: a video rendering module, a 2D graphical view rendering module, a reference point module, and an XY coordinate module. The video rendering module is operable for rendering at least the live video stream of the remote assistance request within the first pane. The 2D graphical view rendering module is operable for rendering within the second pane at least (i) a 2D representation of the subject or the second object at the scene, and (ii) the 2D representation of the first object at the scene. The reference point module is operable for establishing the reference point within the content of the live video stream of the remote assistance request and displayed in the first pane. Lastly, the XY coordinate module is operable for establishing an XY coordinate system in the first pane based at least upon the reference point for the live video stream of the remote assistance request.

In an additional embodiment, the reference point comprises at least one of (i) the subject's face determined via a face recognition algorithm applied to an image of the subject in the live video stream and (ii) a remote assistant selected reference point within the content of the live video stream rendered in the first pane. Furthermore, the remote assistant selected reference point can comprise at least one of (i) a reference point on the subject or second object at the scene, (ii) a reference point on the portable device, and (iii) a reference point on the first object. Moreover, the remote assistant selected reference point can further comprise a vertical direction, wherein the vertical direction is selected by modifying a view of the second pane by rotating the view so that the vertical direction of the view corresponds with a central axis of the subject or the second object at the scene.

In yet another embodiment, the one or more remote assistance signals are configured for displaying at least one highlight on the stereoscopic augmented reality glasses to the first responder within the live view of the scene captured by the camera of the AR glasses. The at least one highlight is displayed in response to at least one remote assistant input that comprises the remote assistant selecting an XY coordinate in the live video stream displayed in the first pane of the remote expert graphical user interface. In this embodiment, the at least one highlight is displayed at a matching XY coordinate in the augmented reality glasses as seen by the first responder.

In a still further embodiment, the second pane of the remote assistant graphical user interface includes at least one tab for each of a plurality of types of actions to be carried out in connection with the subject or second object at the scene. Responsive to a remote assistant selecting, via the remote assistant graphical user interface, a given tab in the second pane, the 2D graphical view rendering module renders within the second pane the one or more 2D representation of the first object associated with the given tab available for use by the remote assistant with respect to a corresponding given type of action. For example, one tab may be specific to AED and related actions such as electrode placement, while other tabs may be specific to CPR, triage, or the like.

In one embodiment, the portable device comprises a portable medical device that includes at least one of an automated external defibrillator (AED), a cardiopulmonary resuscitation (CPR) metronome, and an electrocardiogram (ECG) monitor. The one or more 2D representation of the first object can correspond with one or more of (i) a first responder's hand, hands, or other first responder body part, and (ii) at least one item of the portable device. In addition, the one or more 2D representation of the at least one item of the portable device can be further representative of at least one selected from the group consisting of: AED pad placement, CPR compression placement, and ECG sensor placement. Furthermore, the remote assistance workstation can comprise a display device, wherein the display device includes a touch screen device for receiving the remote assistance inputs.

According to another aspect, a method comprises steps for providing remote assistance via a remote assistance workstation and a portable device, wherein the portable device comprises at least a pair of stereoscopic augmented reality glasses. The portable device is for use by a first responder to carry out at least one action using a first object at a scene in connection with at least one of a subject and a second object at the scene. In particular, the method comprises at least the three steps of operatively coupling, rendering and receiving, and generating.

The first step includes operatively coupling, via a communications module, the remote assistance workstation to the portable device, in response to a remote assistance request initiated from the portable device. The remote assistance request includes at least a live video stream captured via a camera of the stereoscopic augmented reality glasses at the scene.

The second step includes rendering, via a user interface module, a remote assistant graphical user interface on a display device and receiving remote assistant inputs from a remote assistant. The remote assistant graphical user interface includes at least (i) a first pane for displaying the live video stream of the remote assistance request, and (ii) a second pane for displaying a 2D representation of the first object at the scene. The rendered 2D representation is moveable within the second pane in response to one or more remote assistant inputs, wherein remote assistant graphical user interface further renders within the first pane a corresponding at least one item of 3D virtual content, corresponding to the 2D representation of the first object at the scene, relative to at least a reference point within the first pane. The reference point is based upon a content of the live video stream.

The third step includes generating, via a controller, one or more remote assistance signals to be output, via the communications module, to the portable device for displaying the at least one item of 3D virtual content on the stereoscopic augmented reality glasses to the first responder within a live view of the scene as is captured by the camera. The at least one item of 3D virtual content appears at a correct location with respect to the reference point within the live view in response to the one or more remote assistant inputs moving the 2D representation of the first object at the scene within the second pane of the remote assistant graphical user interface, for assisting the first responder to carry out the at least one action in connection with the subject or the second object at the scene.

In another aspect, the method includes wherein generating, via the controller, further comprises generating one or more remote assistance signals for displaying at least one highlight on the stereoscopic augmented reality glasses to the first responder within the live view of the scene captured by the camera, in response to at least one remote assistant input that comprises the remote assistant selecting an XY coordinate in the live video stream displayed in the first pane of the remote expert graphical user interface, further wherein the at least one highlight is displayed at a matching XY coordinate in the augmented reality glasses as seen by the first responder.

In yet another aspect, the method includes wherein the reference point comprises one selected from the group consisting of (i) a reference point of the subject's face determined via a face recognition algorithm applied to an image of the subject in the live video stream rendered in the first pane, and (ii) a remote assistant selected reference point within the content of the live video stream rendered in the first pane. The remote assistant selected reference point further comprises at least one of (i) a reference point on the subject or second object at the scene, (ii) a reference point on the portable device, and (iii) a reference point on the first object, and wherein selecting the remote assistant reference point further comprises modifying a view of the second pane by rotating the view so that a vertical direction of the view corresponds with a central axis of the subject or the second object at the scene.

In a further embodiment of the present disclosure, a non-transitory computer-readable medium is embodied with instructions that, when executed by a processor, cause the processor to carry out the method as discussed herein.

In a still further embodiment, a remote assistance system comprises a remote assistance workstation as discussed herein; and a portable device. The portable device comprises at least a pair of stereoscopic augmented reality glasses and the first object at the scene comprises one or more of (i) a first responder's hand, hands, or other first responder body part, and (ii) at least one item, further wherein the portable device is for use by a first responder to carry out at least one action in connection with at least one of a subject and a second object at a scene. The portable device further comprises a communications module configured for communicating with the remote assistance workstation. In addition, the at least one item comprises at least one workpiece for use by the first responder in connection with carrying out the at least one action on the subject or second object at the scene. Furthermore, the at least a pair of stereoscopic augmented reality glasses to be worn by the first responder includes a camera for capturing real-time images of the subject or second object at the scene.

Still further advantages and benefits will become apparent to those of ordinary skill in the art upon reading and understanding the following detailed description.

The embodiments of the present disclosure may take form in various components and arrangements of components, and in various steps and arrangements of steps. Accordingly, the drawings are for purposes of illustrating the various embodiments and are not to be construed as limiting the embodiments. In the drawing figures, like reference numerals refer to like elements. In addition, it is to be noted that the figures may not be drawn to scale.

FIG. 1 is a block diagram view of a remote assistance workstation with a user interface for providing remote assistance with spatial placement tasks and a portable device, wherein the portable device comprises at least a pair of stereoscopic augmented reality (AR) glasses for use by a first responder to carry out at least one action using a first object at a scene in connection with a subject or a second object at the scene, according to an embodiment of the present disclosure;

Figure 6:
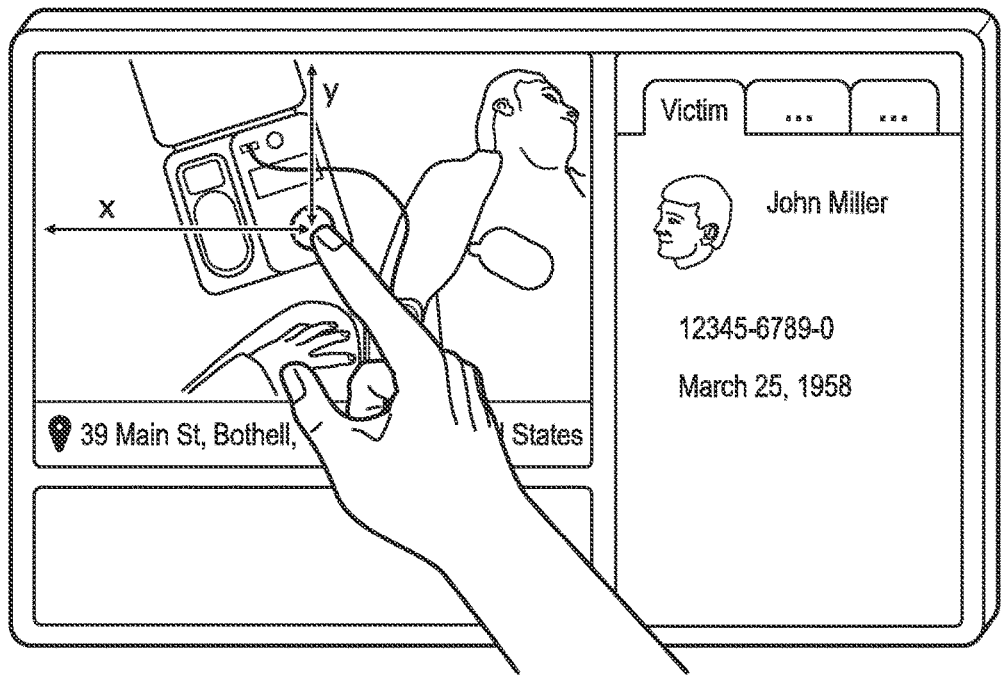
FIG. 6 is a combined image and corresponding annotation view of the first and second panes of the remote assistance workstation graphical user interface, showing remote assistant inputs of an (x,y) coordinate selection received within the first pane of the graphical user interface, according to an embodiment of the present disclosure.
Figure 6:
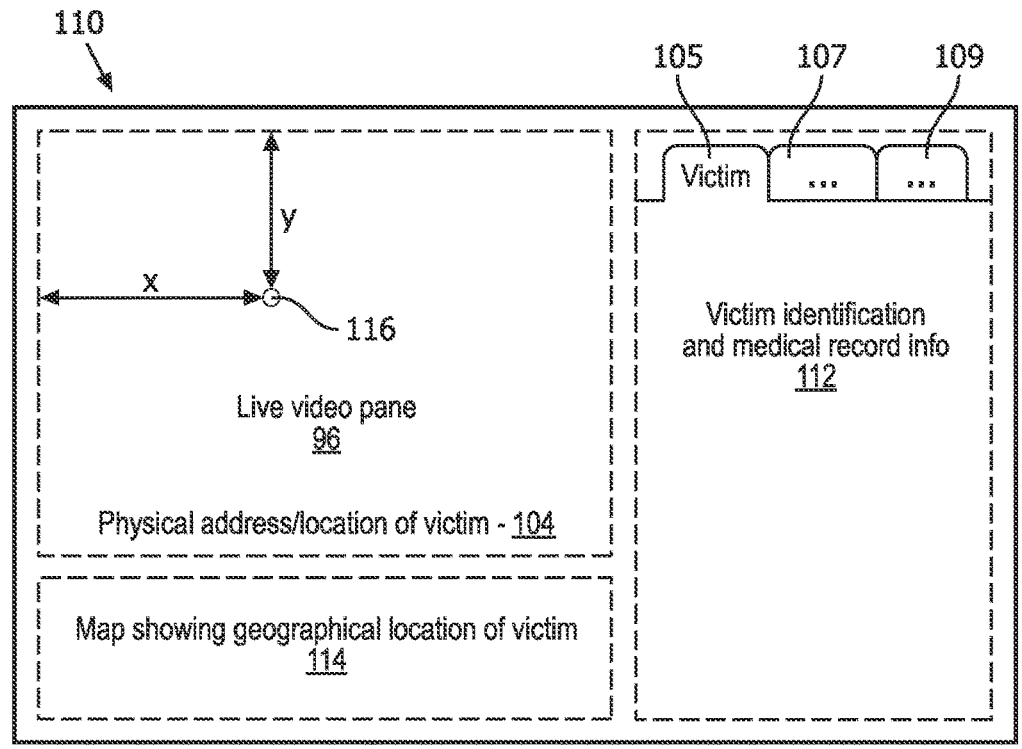
Figure 7:
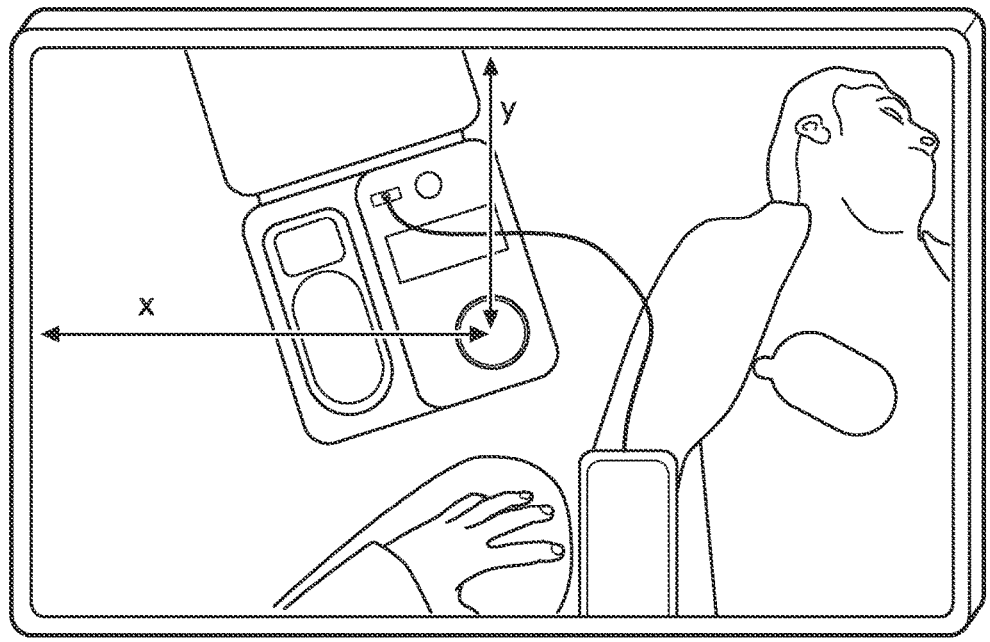
Figure 7:
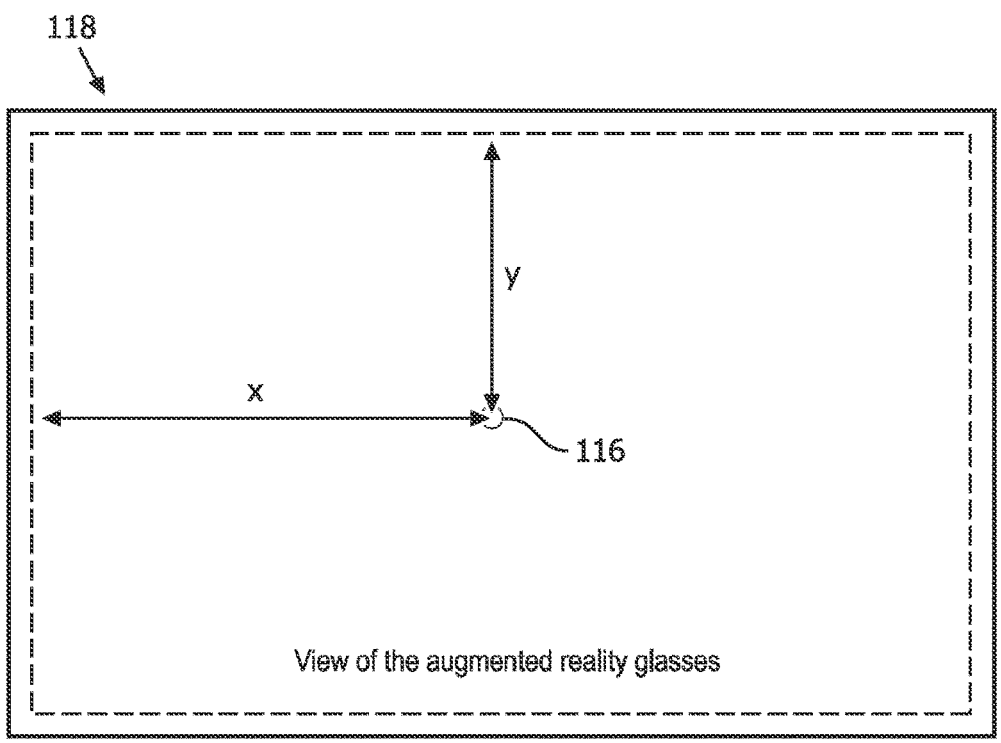
Figure 8:
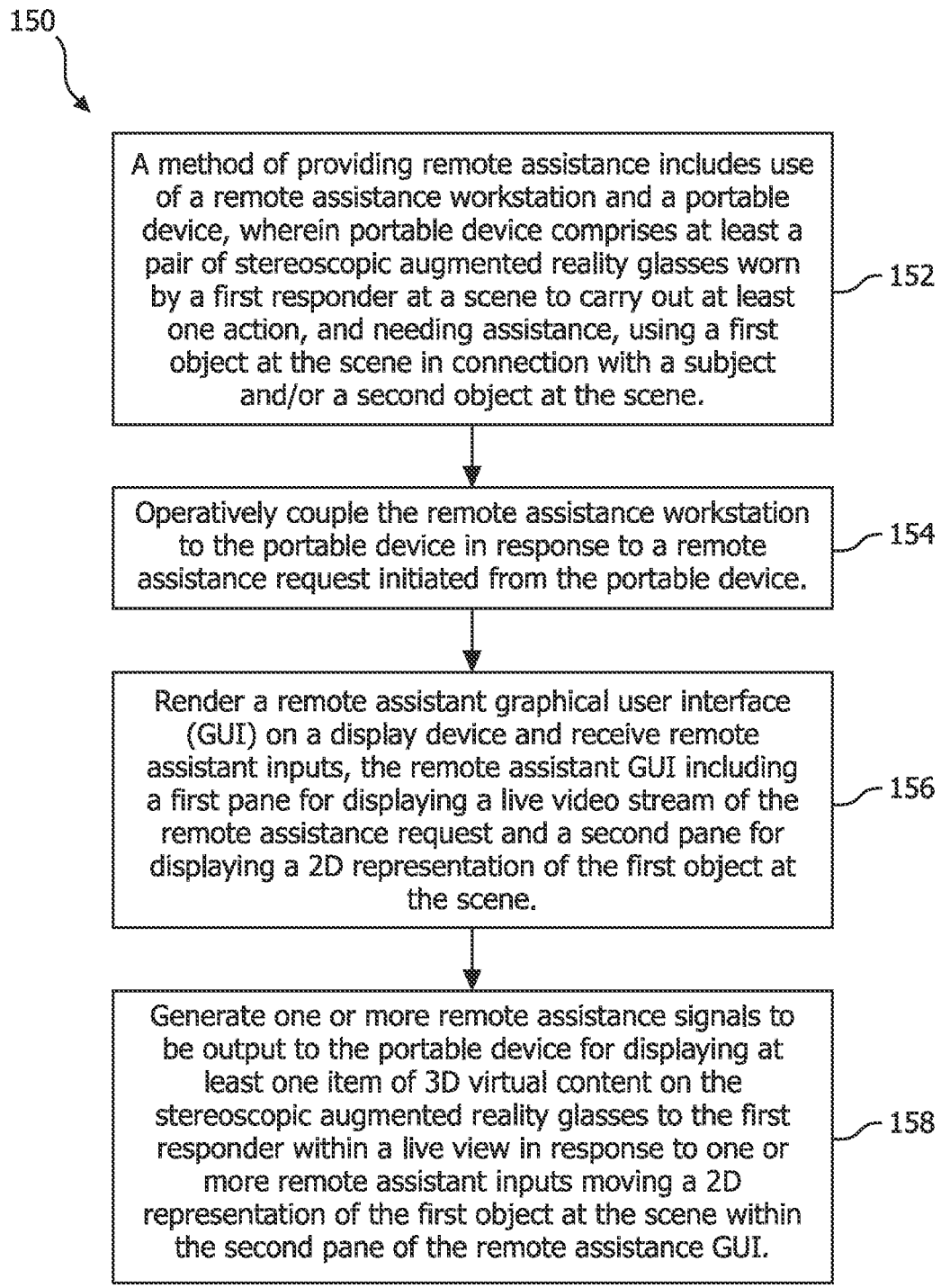

FIG. 7 is a combined image and corresponding annotation view as displayed in augmented reality glasses of a first responder using the portable device with a subject at a scene, showing placement of a highlight at a corresponding (x,y) coordinate per the remote assistant input in the first pane of the graphical user interface of FIG. 6, according to an embodiment of the present disclosure; and FIG. 8 is a flow diagram view of a method for providing remote assistance with spatial placement tasks via a user interface of a remote assistance workstation and a portable device, wherein the portable device comprises at least a pair of stereoscopic augmented reality glasses for use by a first responder to carry out at least one action using a first object at a scene in connection with a subject or a second object at the scene, according to an embodiment of the present disclosure.

The embodiments of the present disclosure and the various features and advantageous details thereof are explained more fully with reference to the non-limiting examples that are described and/or illustrated in the drawings and detailed in the following description. It should be noted that the features illustrated in the drawings are not necessarily drawn to scale, and features of one embodiment may be employed with other embodiments as the skilled artisan would recognize, even if not explicitly stated herein. Descriptions of well-known components and processing techniques may be omitted so as to not unnecessarily obscure the embodiments of the present disclosure. The examples used herein are intended merely to facilitate an understanding of ways in which the embodiments of the present may be practiced and to further enable those of skill in the art to practice the same. Accordingly, the examples herein should not be construed as limiting the scope of the embodiments of the present disclosure, which is defined solely by the appended claims and applicable law.

It is understood that the embodiments of the present disclosure are not limited to the particular methodology, protocols, devices, apparatus, materials, applications, etc., described herein, as these may vary. It is also to be understood that the terminology used herein is used for the purpose of describing particular embodiments only, and is not intended to be limiting in scope of the embodiments as claimed. It must be noted that as used herein and in the appended claims, the singular forms "a," "an," and "the" include plural reference unless the context clearly dictates otherwise.

Unless defined otherwise, all technical and scientific terms used herein have the same meanings as commonly understood by one of ordinary skill in the art to which the embodiments of the present disclosure belong. Preferred methods, devices, and materials are described, although any methods and materials similar or equivalent to those described herein can be used in the practice or testing of the embodiments.

As will be appreciated from the disclosure herein, with the advent of augmented reality (AR) glasses, there is much interest in applications which allow the wearer to consult a remote expert. Because augmented reality glasses feature a camera, a live view of this camera can be forwarded via an internet link, or other suitable communications link, to the remote expert. Typically, the wearer of the AR glasses is "hands-on" present at a scene. The remote expert cannot physically do anything in person at the scene; however the remote expert generally has more knowledge or access to resources. As a result, the remote expert can ask the person present at the scene to do certain things and guide him or her through a procedure, for example, in the case of a medical emergency.

A number of advantageous benefits exist, via the remote assistance workstation, method and system with a user interface of the present disclosure for providing remote assistance to a first responder with spatial placement tasks via augmented reality glasses. The benefits include one or more of: the person present at the scene can be "less trained"; the remote expert can offer task support; the remote expert can offer emotional support; and with the help of the remote expert, problems may get solved without having to visit the scene a second time. In one example, a first responder in an emergency situation can connect to an expert in a 911 emergency response team, via the AR glasses and remote expert user interface. In another example, a field engineer carrying out maintenance or repair work can connect to a back office to consult an expert who is more knowledgeable on a certain machine, a certain procedure, availability of components, etc.

As will be understood from the disclosure herein, the embodiments of the present disclosure make use of stereoscopic augmented reality (AR) glasses, which is to be differentiated from "glasses with an auxiliary display." With respect to "glasses with an auxiliary display" (e.g., Google™ Glass), the auxiliary display, often positioned in the top right hand corner of the visual field, can show the video stream captured by the camera in the glasses. The display exists next to the user's actual view of the real world: it is not possible to put virtual objects directly onto the user's view of the real world. As a result, it is possible for a remote expert to highlight elements in the camera image, but to the person wearing the glasses, these appear in the auxiliary display, not in his or her direct view of the physical world. The drawback then is that there is "indirection": the user needs to check at the auxiliary display to see what element is highlighted by the remote expert and thereafter look for the corresponding element in his or her actual, physical surrounding.

With respect now to stereoscopic augmented reality (AR) glasses, the essence of stereoscopic AR glasses is that through displays directly in front of the user's eyes, virtual content can be co-located with the physical world. That is, virtual content can be displayed in such a way that to the user it appears at a particular location in his or her physical surroundings, like a computer generated holograph. An advantage of such AR glasses is that the remote assistant or expert can move virtual content to a particular 3D location (i.e., move virtual content to a particular location in the 2D representation of the 3D scene, which is then presented or made visible in the AR glasses of the first responder) to direct the attention of the person at the scene, indicate direction, show what should go where etc., for the particular remote assistance application (e.g., in an emergency situation). One problem is that when the live video feed from the camera in the AR glasses is displayed as an image on the remote expert's display, it moves about with the head-position of the person at the scene. This makes it impossible for the remote expert to manipulate virtual content directly in the live view. At the same time, it is very useful for the remote assistant or expert to point a virtual cursor at something in the live view, in full confidence that the person at the scene sees the virtual pointer on top of the same element in his visual field.

In view of the above, the inventors have invented a remote assistant graphical user interface (GUI) for the remote assistant or expert which contains two panes. The first pane shows a live view from the AR glasses. The second pane shows a two dimensional (2D) view on the 3D scene in which the remote assistant or expert can move about virtual content. That is, the second pane shows a graphical representation with a 2D view of the remote scene (i.e., for a given orientation, such as a top view, side view, etc.) and various moveable virtual objects. The remote assistant GUI advantageously offers the remote assistant at least two modes to communicate information to the person or first responder present at the scene.

In one mode, the remote assistant can highlight any part in the live video stream in the first pane through selecting, e.g., via touching a touch screen display having the live video stream in the first pane displayed thereon, an (x,y) coordinate and exactly the same part will be highlighted in the stereoscopic AR glasses for the person wearing the AR glasses to see. The virtual highlight is stationary with respect to the frame of the live view pane (i.e., for the expert) as well as with respect to the AR glasses. However, this mode only works if the "person at the scene" holds his or her head still temporarily, as otherwise the view on the scene will "slide" relative to the virtual highlight.

In another mode, the remote assistant can select and move (i.e., drag) one or more desired virtual content around in the 2D representation of the scene. Because the virtual content, as moved in the second pane of the user interface by the remote assistant, is positioned relative to a fixed reference point in the 3D scene, it does not matter if the person wearing the AR glasses moves his or her head: the remote assistant can move the virtual content within the second pane without the virtual content jumping about within the live video view of the first pane with the movements of the augmented reality glasses. As the remote assistant moves the virtual content in the second pane, the remote assistant can see how the virtual content will appear to the "person at the scene," that is, via the first pane showing the live video stream with the 3D virtual content included therein.

According to another embodiment of the present disclosure, a remote assistance system includes augmented reality goggles (e.g., AR headsets) at one end, and a computer display (e.g., a remote processing device, workstation, etc.) at the other. The computer display has a 3D pane showing the video at the one end and a 2D pane with graphic representations of items in the 3D pane (e.g., representative of items at the scene, medical equipment at the scene, or a portable medical apparatus at the scene). The remote assistant manipulates items in the 2D pane, which are automatically applied and maintained at the correct position in the 3D pane with respect to a given reference point within the scene of the video displayed in the 3D pane and that corresponds to an actual point or location at the scene.

In another embodiment, a method for a person (e.g., a first responder) present at the scene using augmented reality headsets (AR headsets) to connect to a remote assistant includes the remote assistant making use of a remote assistant graphical user interface. The remote assistant graphical user interface (GUI) comprises two panes: a first pane with a live video stream view from the camera in the AR glasses; and a second pane showing a representation with a 2D view of the remote scene and various moveable virtual objects. The remote assistant GUI offers the remote assistant or expert two modes to communicate the information to the 'person present at the scene'. In one mode, the remote assistant can highlight any part in the live video stream view in the first pane and exactly the same part will be highlighted in the glasses of the person wearing the AR glasses. In another mode, the remote assistant can select and move (i.e., drag) one or more desired virtual content around in the 2D representation of the scene. Because the virtual content is positioned relative to a fixed reference point in the live video image of the scene, it does not matter if the person wearing the AR glasses moves his or her head in this case.

In the following discussion with reference to FIGS. 1-8, the embodiments of the present disclosure will be discussed in the context of an actual use case involving remote assistance in a sudden cardiac arrest situation. However, the embodiments of the present disclosure can also be applied to other types of remote assistance situations, as appropriate for the given situation.

Figure 1:
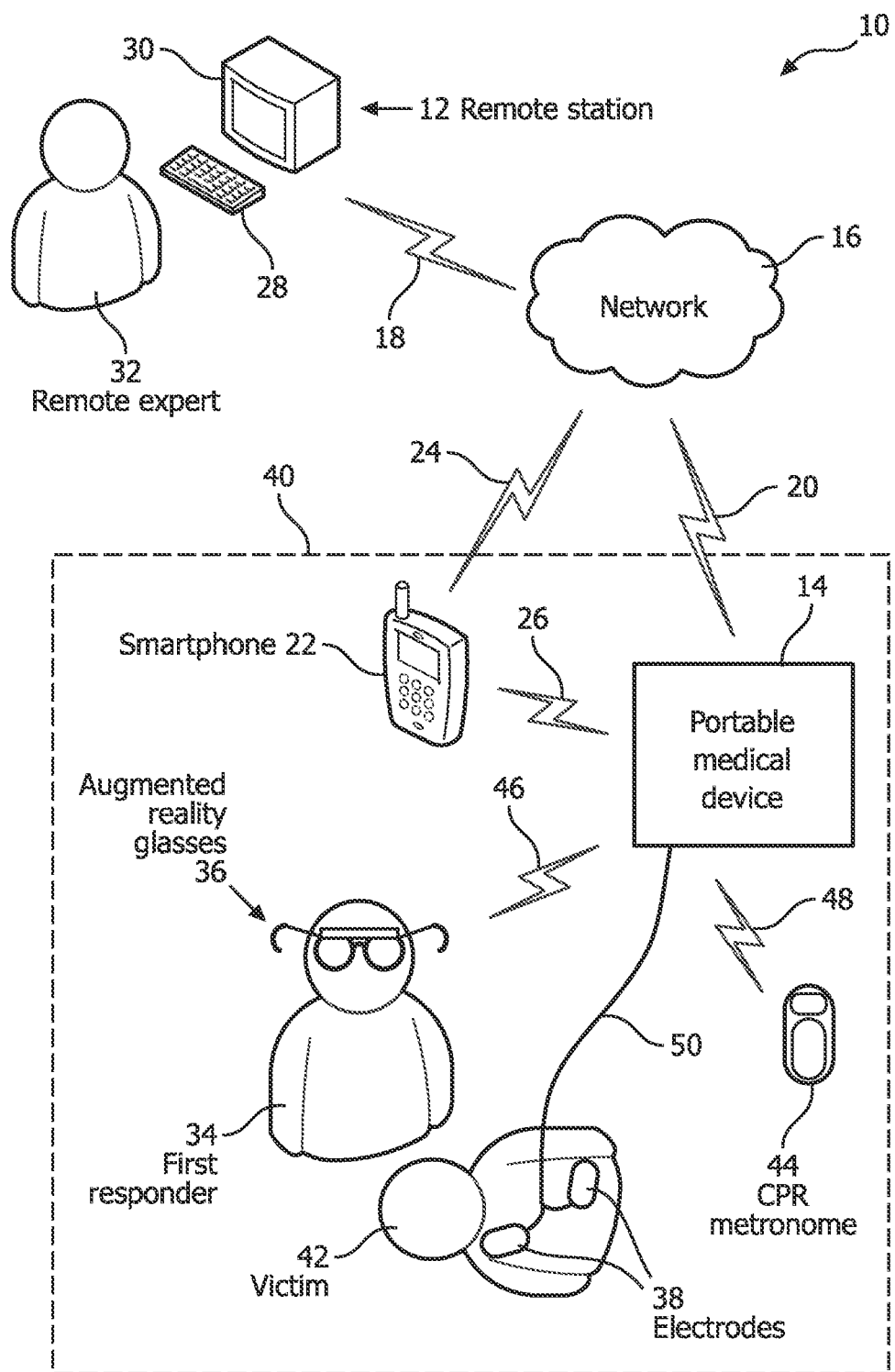

Turning now to FIG. 1, there is shown a block diagram view of a remote assistance system 10 that comprises a remote assistance workstation 12 and a portable device 14 coupled to each other via a communications link 16. The communication link 16 can comprise any suitable network, e.g., a wireless network, internet, or other known or later developed network, for directly or indirectly communicating between the remote assistance workstation 12 and the portable device 14. For example, the communications link 16 can be directly coupled between the remote assistance workstation 12 and the portable device 14 as indicated by reference numerals 18 and 20. Similarly, the communications link 16 can be indirectly coupled, e.g., via a smartphone 22 located within a given immediate proximity of the portable medical device 14, between the remote assistance workstation 12 and the portable device 14 as indicated by reference numerals 18, 24 and 26. Detailed specifics of the communication between the various devices and components as discussed herein is preferably accomplished using suitable techniques known in the art, and thus are not discussed further herein.

The remote assistance workstation 12 includes at least one input/output device 28 (e.g., a keyboard, mouse, touch input, etc.) and a display 30 for use by a remote assistant 32. The remote assistance workstation 12 further includes a user interface, as will be discussed further herein below, for providing remote assistance to a first responder 34 with spatial placement tasks using the portable device 14.

With reference still to FIG. 1, the portable device 14 comprises at least a pair of stereoscopic augmented reality (AR) glasses 36 for use by the first responder 34 to carry out at least one action using a first object 38 (e.g., a pair of AED electrodes, the first responder's hand, hands, etc.) at a scene 40 in connection with a subject 42 (e.g., a victim) or a second object (not shown) at the scene. In one embodiment, the portable device 14 comprises a portable medical device that includes at least one of an automated external defibrillator (AED), a cardiopulmonary resuscitation (CPR) metronome, and an electrocardiogram (ECG) monitor. In addition, the first object 38 at the scene 40 can comprise one or more of (i) a first responder's hand, hands, or other first responder body part, and (ii) at least one item (i.e., electrodes or CPR metronome) of the portable device. In FIG. 1, the portable device 14 can further include a CPR metronome 44. Communications between the augmented reality glasses 36 and the portable device 14 is indicated by reference numeral 46. Similarly, communications between the portable device 14 and the CPR metronome 44 is indicated by reference numerals 48. In addition, in the case of AED electrodes 38, the AED electrodes are coupled to the portable device 14 via suitable signal/power lines 50. Specific details of the communication and signal/power lines between the various devices and components as discussed herein is preferably accomplished using suitable techniques known in the art, and thus are not discussed further herein.

In operation, the 'person at the scene' or first responder 34 wears the stereoscopic augmented reality glasses 36. A data connection is established between the AR glasses 36 and the remote assistance workstation 12 attended by a remote expert or assistant 32. The remote assistant 32 utilizes a remote assistant graphical user interface, as will be discussed further herein, which includes at least two panes, the first pane showing a live video stream from the AR glasses 36 and the second pane showing a graphical 2D view of the scene (or portion thereof and for a given orientation, e.g., top view, side view, etc.) in which 2D representations of 3D virtual objects can be selected and moved about. In other words, the second pane contains an illustrative 2D graphical view of the scene with respect to an actual subject or object in the scene and a reference point on the actual subject or object in the scene. The 2D representations of 3D virtual objects can be selected and moved around within the second pane by the remote assistant, further as will be discussed herein.

Figure 2:
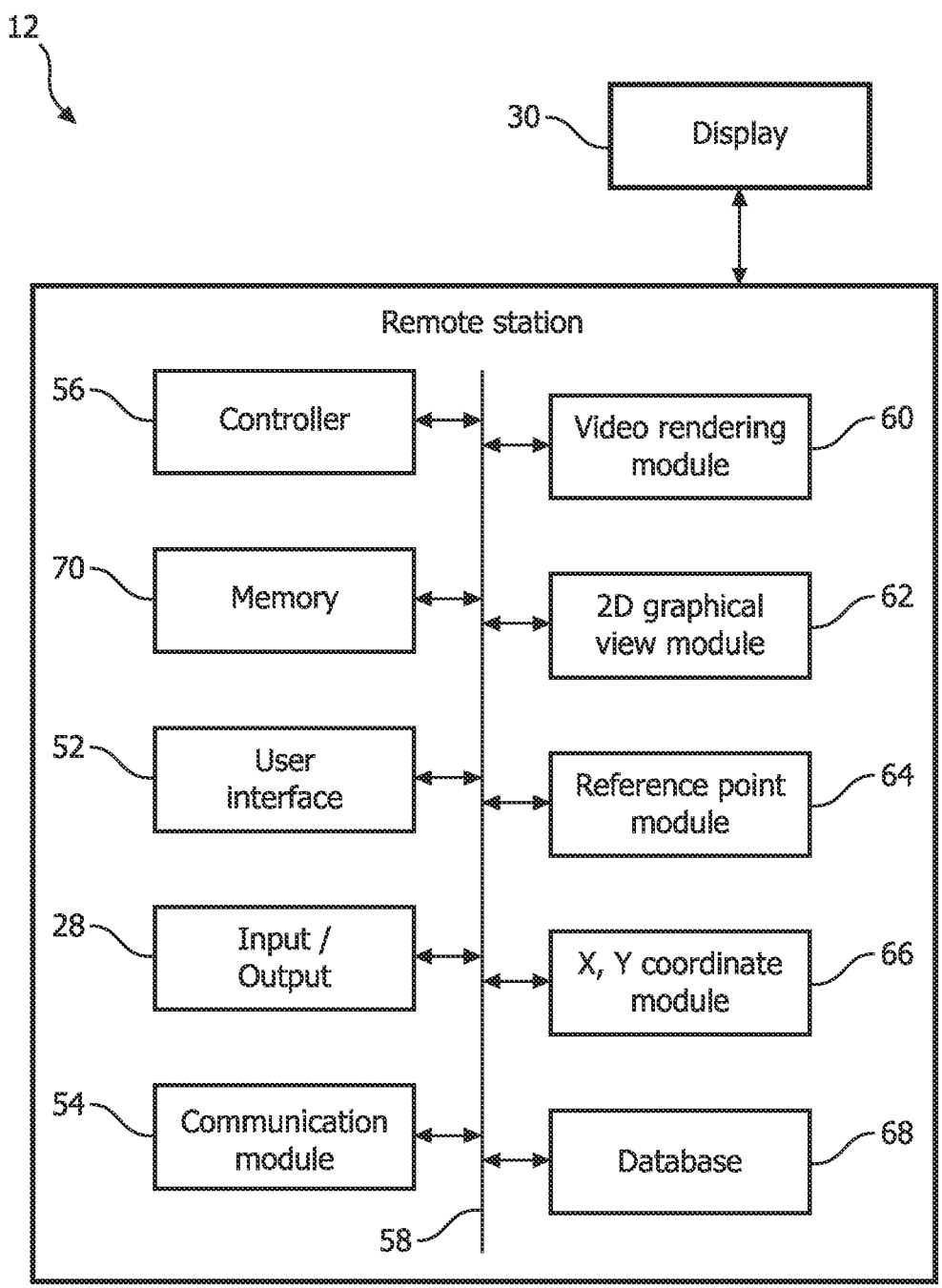
FIG. 2 is a block diagram view of a remote assistance workstation with a user interface for remote assistance with spatial placement tasks in further detail according to an embodiment of the present disclosure.

With reference now to FIG. 2, a block diagram view of the remote assistance workstation 12 with a user interface for remote assistance with spatial placement tasks in further detail is shown. The remote assistance workstation 12 comprises at least a user interface 52, a communications module 54 (e.g., configured for communicating with one or more of the portable medical device 14 and the smartphone 22 located within a given immediate proximity of the portable device), and a controller 56. In one embodiment, the user interface 52 is configured for at least obtaining remote assistant inputs from the remote assistant 32 (FIG. 1), i.e., via input/output device 28. The user interface 52 comprises at least a graphical user interface operatively coupled to at least the controller 56, via signal lines 58, for use in connection with a given remote assistance situation, e.g., during an emergency, as discussed further herein. In addition, user interface 52 can further comprise at least one selected from the group consisting of an input/output device, a tactile device, a touch screen, an optical display, a microphone, a keypad, a keyboard, a pointing device, an image capture device, a video camera, an audio input/output device, and any combination thereof, determined as appropriate according to the requirements of a given remote assistance implementation and/or application. Furthermore, in one embodiment, controller 56 comprises one or more of a microprocessor, microcontroller, field programmable gate array (FPGA), integrated circuit, discrete analog or digital circuit components, hardware, software, firmware, or any combination thereof, for performing various functions as discussed herein, further according to the requirements of a given portable medical device implementation and/or application. Controller 56 can further comprise one or more of the various modules as discussed herein. Additional details regarding the controller 56 will be provided herein below with reference to the Figures.

With reference still to FIG. 2, the remote assistant workstation 12 can further comprise one or more of a video rendering module 60, a 2D graphical view rendering module 62, a reference point module 64, and an XY coordinate module 66. The video rendering module 60 is operable for rendering at least the live video stream of the remote assistance request within a first pane of the remote assistant graphical user interface. The 2D graphical view rendering module 62 is operable for rendering within the second pane at least (i) a 2D representation of the subject or the second object at the scene, and (ii) the 2D representation of the first object at the scene. The reference point module 64 is operable for establishing the reference point within the content of the live video stream of the remote assistance request and displayed in the first pane. Lastly, the XY coordinate module 66 is operable for establishing an XY coordinate system in the first pane based at least upon the reference point for the live video stream of the remote assistance request. The remote assistance workstation 12 can still further comprise one or more of a database 68 and memory 70. Each of the database 68 and memory 70 is operatively coupled to at least the controller 56, e.g., via signal lines 58. In one embodiment, the modules 60-70 can comprise one or more of an integrated circuit, discrete analog or digital circuit components, hardware, software, firmware, or any combination thereof, for performing various functions as discussed herein, further according to the requirements of a given remote assistant workstation implementation and/or application. In addition, one or more of the modules 60-70 can further comprise various combinations of one or more of the various modules.

Figure 3:
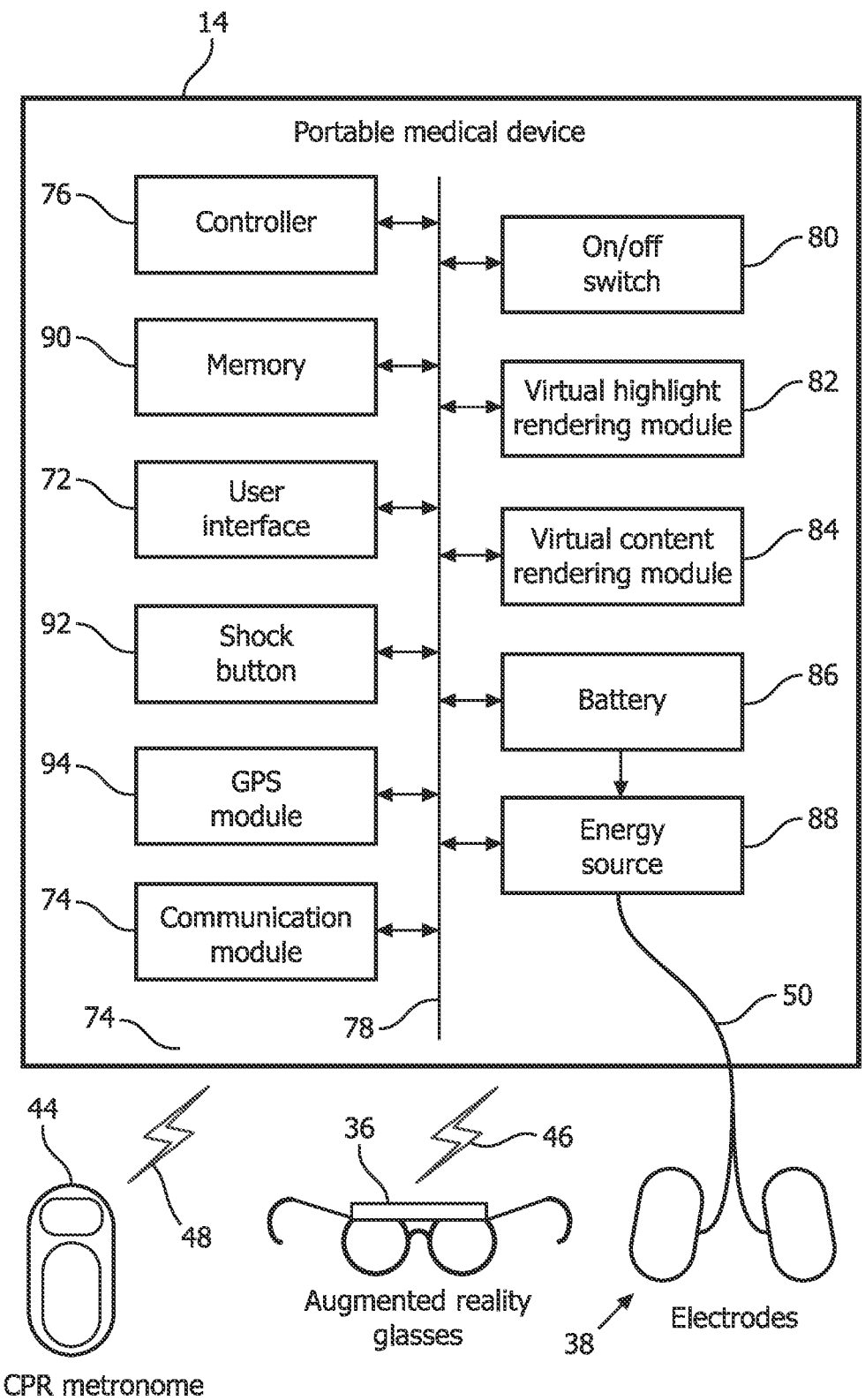
FIG. 3 is a block diagram view of a portable device for use by a first responder to carry out at least one action using a first object at a scene in connection with a subject or a second object at the scene according to an embodiment of the present disclosure.

With reference now to FIG. 3, a block diagram view of a portable device 14 for use by a first responder 34 to carry out at least one action using a first object at a scene 40 in connection with a subject 42 or a second object at the scene according to an embodiment of the present disclosure is shown. In one embodiment, the portable device 14 comprises a portable medical device that includes at least a user interface 72, a communications module 74, and a controller 76. The user interface 72 is configured for at least initiating a request for remote assistance and comprises any suitable user interface operatively coupled to at least the controller 76, via signal lines 78, for use in connection with receiving remote assistance during an emergency situation, as discussed further herein. For example, user interface 72 can comprise at least one selected from the group consisting of an input/output device, a tactile output device, a touch screen, an optical display, a microphone, a keypad, a keyboard, a pointing device, an image capture device, a video camera, an audio output device, and any combination thereof, determined as appropriate according to the requirements of a given portable medical device implementation and/or application.

The communications module 74 is configured for communicating with at least one of (i) the remote assistance workstation 12 and (ii) a smartphone 22 located within a given immediate proximity of the portable medical device. The communications module 74 is further for receiving, via at least one of the remote assistance workstation 12 or the smartphone 22 communicating with the remote assistant workstation, in response to the first responder's remote assistance request, one or more remote assistance signals from the remote assistance workstation 12. The one or more remote assistance signals from the remote assistance workstation 12 contain information for displaying at least one item of 3D virtual content on the stereoscopic augmented reality glasses 36 to the first responder 34 within a live view of the scene 40 as is captured by a camera of the AR glasses 36. In addition, the at least one item of 3D virtual content appears at a correct location with respect to a reference point within the live view in response to the one or more remote assistant inputs moving a 2D representation of the first object at the scene within a corresponding 2D representation pane of a remote assistant graphical user interface of the remote assistance workstation 12, as is discussed further herein, for assisting the first responder to carry out the at least one action using the first object in connection with the subject or the second object at the scene.

Communication between the communication module 74 of the portable medical device 14 and the remote assistant workstation 12 is indicated by reference numerals 18 and 20, including network 16 (FIG. 1). Communication between the communication module 74 of the portable medical device 14 and the remote assistance workstation 12 can also occur via smartphone 22, and is indicated by reference numerals 18, 24 and 26, including network 16 (FIG. 1). Communication between the communication module 74 of the portable medical device 14 and the AR glasses 36 is indicated by reference numeral 46. Communication between the communication module 74 of the portable medical device 14 and the AR glasses 36 is indicated by reference numeral 46. Communication between the communication module 74 of the portable medical device 14 and the CPR metronome 44 is indicated by reference numeral 48. In each instance, communication between the various devices and components as discussed herein is preferably accomplished using suitable techniques known in the art, and thus are not discussed further herein.

The controller 76 operatively couples to the user interface 72 and the communication module 74 via suitable signal lines, indicated via reference numeral 78. Controller 76 is configured for generating, in response to the one or more remote assistance signals from the remote assistant workstation 12, control signals output to the AR glasses 36 for displaying at least one item of 3D virtual content on the AR glasses 36 to the first responder 34 within a live view of the scene 40 as is captured by the camera portion of the AR glasses 36. Accordingly, the first responder receives remote assistance to carry out the at least one action using the first object in connection with the subject or the second object at the scene. In one embodiment, controller 76 comprises one or more of a microprocessor, microcontroller, field programmable gate array (FPGA), integrated circuit, discrete analog or digital circuit components, hardware, software, firmware, or any combination thereof, for performing various functions as discussed herein, further according to the requirements of a given portable medical device implementation and/or application. Controller 76 can further comprise one or more of the various modules as discussed herein. Additional details regarding the controller 76 will be provided herein below with reference to the Figures.

With reference still to FIG. 3, the portable medical apparatus 14 can further comprise one or more of an ON/OFF switch 80, a virtual highlight rendering module 82, a virtual content rendering module 84, a battery 86, an energy source 88, memory 90, shock button 92 (e.g., for activating the administration of a shock via AED pad electrodes), and GPS module 94. Each of the one or more of the ON/OFF switch 80, virtual highlight rendering module 82, virtual content rendering module 84, battery 86, energy source 88, memory 90, shock button 92, and GPS module 94 is operatively coupled to at least the controller 76, e.g., via signal lines 78. The ON/OFF switch 80 comprises any suitable switch for powering the portable medical apparatus 70 between ON and OFF. The virtual highlight rendering module 82 comprises any suitable computer program module for rendering a virtual highlight on the AR glasses 36 to the first responder 34 within a live view of the scene 40 as is captured by the camera portion of the AR glasses 36. The virtual content rendering module 82 comprises any suitable computer program module for rendering the at least one item of 3D virtual content on the AR glasses 36 to the first responder 34 within the live view of the scene 40 captured by the camera portion of the AR glasses 36. It is understood that the described modules may be computer program modules which are rendered in a non-transitory computer-readable medium. Portable medical device 14 can further comprise an audio speaker (not shown) for a given implementation and/or portable medical device application.

In one embodiment, battery 86 can comprise any suitable power source or power supply for a given portable medical device implementation and/or application. In addition, energy source 88 can comprise any suitable power source or power supply for a given portable medical device implementation and/or application. For example, for a portable medical device comprising an AED device, the energy source 88 can comprise high voltage capacitor suitable for storing energy effective in defibrillating shocks, where the capacitor is charged by battery 86 through a charging circuit (not shown). Furthermore, memory 90 can comprise any suitable memory device, operatively coupled to at least the controller 76, for at least storing information thereto, and further for at least subsequently retrieving the information there from.

The global positioning system module 94 comprises any suitable GPS module configured for determining a global position of the portable emergency medical apparatus 14. The controller 76 is further configured for determining that the smartphone is located within a given immediate proximity of the portable emergency medical apparatus based on the global position of the portable emergency medical apparatus 14 and a global position of the smartphone 22.

The portable medical apparatus 14 can further comprise a pair of AED pad electrodes 38 operatively coupled to energy source 88, for administration of an electrical shock during use of the portable medical device 14 as an AED device. The portable medical apparatus 14 can further comprise a pair of augmented reality glasses 36 to be worn by a first responder or rescuer, e.g., in performing AED and/or CPR during an emergency treatment. The augmented reality glasses 36 are operatively coupled via suitable communication link 46 (e.g., a near field communication (NFC), Bluetooth™, or other suitable short-range communication link) with communication module 74 of the portable medical apparatus 14.

Still further, the portable medical apparatus 14 can comprise a CPR metronome 44 to be used by a first responder or rescuer in performing CPR during an emergency treatment. The CPR metronome is operatively coupled via suitable communication link 48 (e.g., a near field communication (NFC), Bluetooth™, or other suitable short-range communication link) with communication module 74 of the portable medical apparatus 14. In one embodiment, the CPR metronome 44 comprises an accelerometer-based CPR metronome. The CPR metronome is configured to take into account chest depth to guide the first responder on how deep to press. In another embodiment, the CPR metronome 44 can comprise an accelerometer-equipped smartphone with a CPR app which takes into account chest depth to guide the first responder on how deep to press, either through information on the live view of the AR glasses 36 and/or through audio guidance. Note that while the above makes reference to accelerometer-based metronome devices, such devices may not always need to be accelerometer-based. Essentially, the metronome device is depth-aware relative to the body. Accordingly, in another embodiment, augmented reality glasses 36 can be used to assist the first responder to establish a position of the CPR metronome or of the first responder's hands for applying pressure, via the remote assistance.

To gain a greater understanding of the embodiments, with reference to FIGS. 1, 2 and 3, let us consider a use case of remote assistance that involves a sudden cardiac arrest situation. The first responder 34 at the emergency scene 40 wears stereoscopic AR glasses 36. The remote medical expert 32 is in a 911 emergency response team. The AR glasses 36 of the first responder 34 connect via the internet to the workstation 12 of the remote medical expert 32. The remote medical expert 32 operates the workstation 12 which includes a graphical user interface with two panes (as will be discussed further herein with reference to FIG. 4). A first pane shows a live video stream captured from the stereoscopic AR glasses of the first responder, and which includes a showing of the victim (i.e., the subject or object in the 3D scene of the live video stream) and the surroundings (i.e., surrounding in the 3D scene of the live video stream). A second pane of the GUI includes a graphical representation of a 2D top view of the victim (i.e., a 2D representation of the subject or object in the 3D scene of the live video stream), containing virtual content which can be selected and moved about within the second pane by the remote medical expert using touch or a pointing device. According to another embodiment, once selected and moved, the virtual content can further be activated/deactivated by the remote expert, via a user input and the workstation controller 56, to appear/disappear respectively within the 3D view of the first pane.

The remote medical expert can communicate information to the first responder in at least two modes, a highlight mode and a virtual content mode. In the highlight mode, the remote medical expert can touch the live video stream in the first pane causing a highlight to appear in the AR glasses of the first responder (as discussed further herein below with reference to FIGS. 6 and 7). In other words, in a highlight mode, responsive to the remote medical expert touching (i.e., selecting) a point within live video displayed in the first pane, the workstation 12, via at least the controller 56 and the X,Y coordinate module 66, outputs a highlight at a corresponding point within the 3D scene which appears in the AR glasses of the first responder. The remote medical expert can also use this highlight mode, via at least the controller 56 and the reference point module 64, to establish a reference point for the virtual content mode, e.g., via a snapshot of the scene including the reference point.

In the virtual content mode, the remote medical expert can select and move virtual content about and activate/deactivate (e.g., make appear/disappear) the virtual content in the 2D pane, i.e., the second pane of the remote assistant graphical user interface. In other words, in the virtual content mode, responsive to the remote medical expert selecting and moving virtual content within the second pane of the graphical user interface relative to a 3D scene reference point, there is a corresponding movement of virtual content rendered in 3D within the live video pane. Furthermore, as used herein, the phrase "movable 2D representation of 3D virtual content" is to be understood as follows. In response to the remote expert selecting and moving the 2D representation of 3D virtual content within the 2D graphical view, there is a corresponding movement of virtual content rendered in 3D within the live video pane (i.e., the first pane) at a location mapped as a function of (i) the 2D representation of the subject or object at the scene and (ii) one or more corresponding reference points within the 2D representation (in the second pane) and live video (in the first pane).

In one embodiment, the 2D representation of 3D virtual content includes content specific to (i.e., relevant to) the given remote assistance situation (e.g., medical emergency—sudden cardiac arrest situation). In addition, the 3D virtual content moves relative to a reference point (e.g., the reference point being the face of the victim) within the live video of the first pane. One example includes selecting and moving virtual outlines (i.e., overlay outlines) indicating where electrode pads of an automatic external defibrillator (AED) should be placed upon the victim at the medical emergency scene. Another example includes selecting and moving a hands icon to indicate where on the victim's chest the first responder should apply pressure for administering CPR compressions/decompressions.

Figure 4:
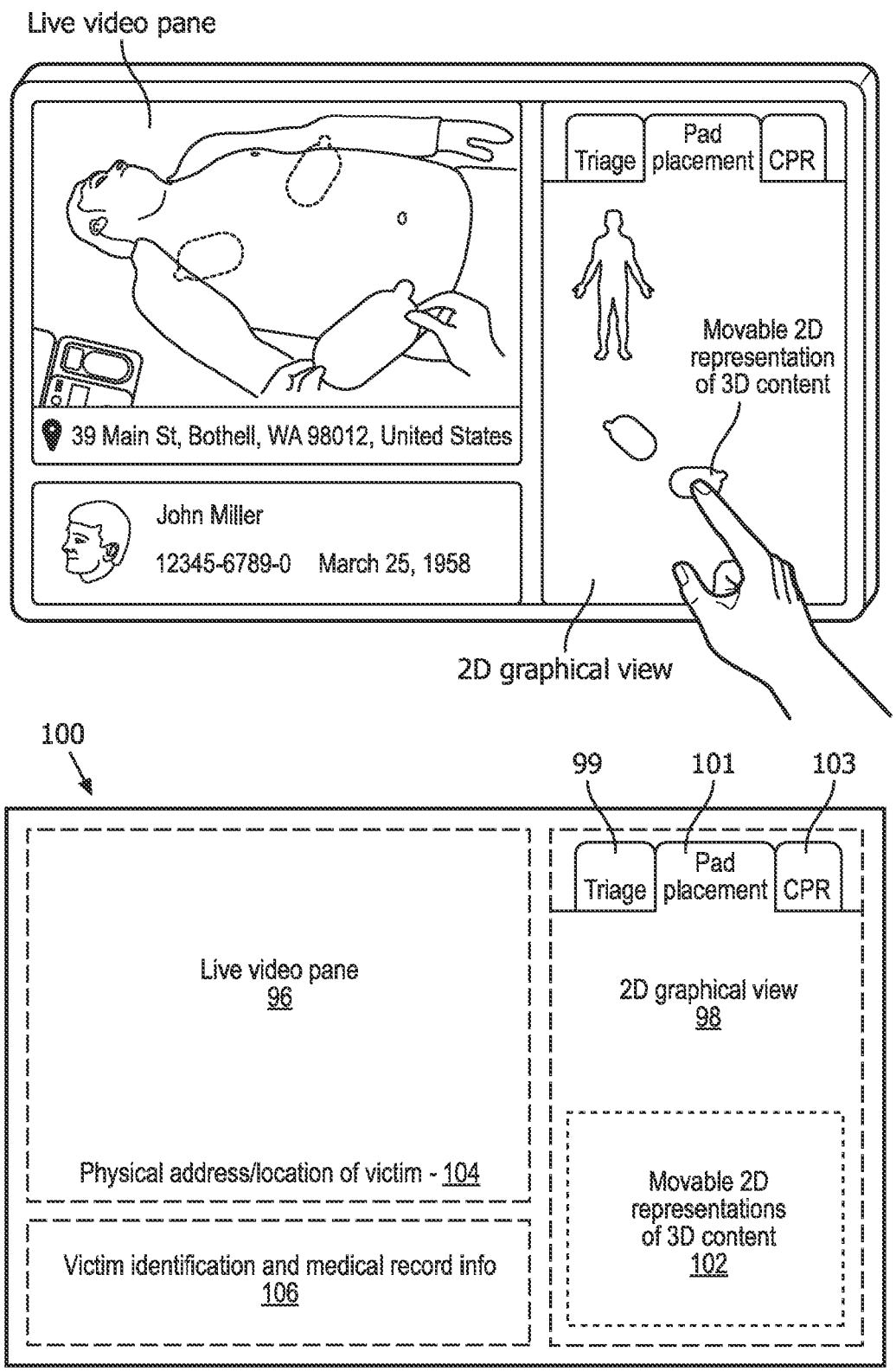
FIG. 4 is a combined image and corresponding annotation view of the first and second panes of the remote assistance workstation graphical user interface, showing remote assistant inputs of movable 2D representations of 3D content being selected and moved within the second pane of the graphical user interface, according to an embodiment of the present disclosure.

With reference now to FIG. 4, there is shown a combined image and corresponding annotation view of the first and second panes, indicated by reference numerals 96 and 98, respectively, of the remote assistance workstation graphical user interface 100, showing remote assistant inputs of movable 2D representations of 3D content, indicated by reference numeral 102, being received in the second pane 98 of the graphical user interface 100, according to an embodiment of the present disclosure. The annotated view has been provided to more clearly illustrate the delineation of the first and second panes, 96 and 98, respectively. In the live video of the first pane 96, the remote assistant 32 views a victim 42 that may require defibrillation, as the first responder 34 prepares to attach the AED electrodes 38 to the victim's chest. As discussed herein, the second pane 98 includes a 2D graphical view, e.g., of the victim at the scene, and movable 2D representations of 3D content 102, e.g., representative of each AED electrode, within the second pane 98.

In addition, with reference still to FIG. 4, in a further embodiment, the second pane 98 of the remote assistant graphical user interface 100 includes at least one tab (99, 101, and/or 103) for each of a plurality of types of actions (e.g. tabs of various folders or types of actions) to be carried out in connection with the subject or second object at the scene. Responsive to a remote assistant selecting, via the remote assistant graphical user interface, a given tab (99, 101 or 103) in the second pane, the 2D graphical view rendering module renders within the second pane the one or more 2D representation of the first object associated with the given tab (99, 101 or 103) available for use by the remote assistant with respect to a corresponding given type of action. For example, in FIG. 4, the 2D graphical view 98 shows an active tab 101 specific to AED and related actions such as electrode placement, while other tabs may be specific to CPR (tab 103), triage (tab 99), or the like.

As shown in FIG. 4, the remote assistant 32 selects and moves each of the electrodes 38 within the 2D graphical view of the second pane 98. Moving the 2D representations of the 3D content within the second pane, e.g., via a touch screen control within the second pane 98 results in a corresponding placement of 3D outlines or overlays of the moveable object on the live video of the first pane 96, so as to provide remote assistance to the first responder 34 with the corresponding spatial placement tasks at the scene. In other words, FIG. 4 illustrates a remote expert positioned at the workstation with two panes, a live video pane showing the video feed from the AR glasses at the scene and a graphical 2D pane with 2D representations of 3D virtual content.

In another embodiment, the second pane can include a staging area (e.g., in an upper portion of the 2D graphical view 98), from which to select 3D virtual content and move the selected 3D virtual content to an active area (e.g., in a lower portion of the 2D graphical view 98), in which the selected and moved 3D virtual content becomes active and also appears within the live video pane. Additional features could also be applied, for example, once a 3D virtual content is selected and moved to the active region, an additional remote assistant input could be used to toggle an appearance/disappearance of the 3D virtual content within the live video pane.

In addition, the first pane 96 may also include a location information insert 104, wherein the insert 104 is indicative of a physical address and/or location of the victim 42 in response to a GPS signal obtained via the GPS module 94 of the portable medical device 14. Still further, the remote assistant graphical user interface 100 can include another pane 106 which presents victim identification information and medical record info to the remote assistant 32, if available, from the portable medical device 14, or from another suitable source.

Figure 5:
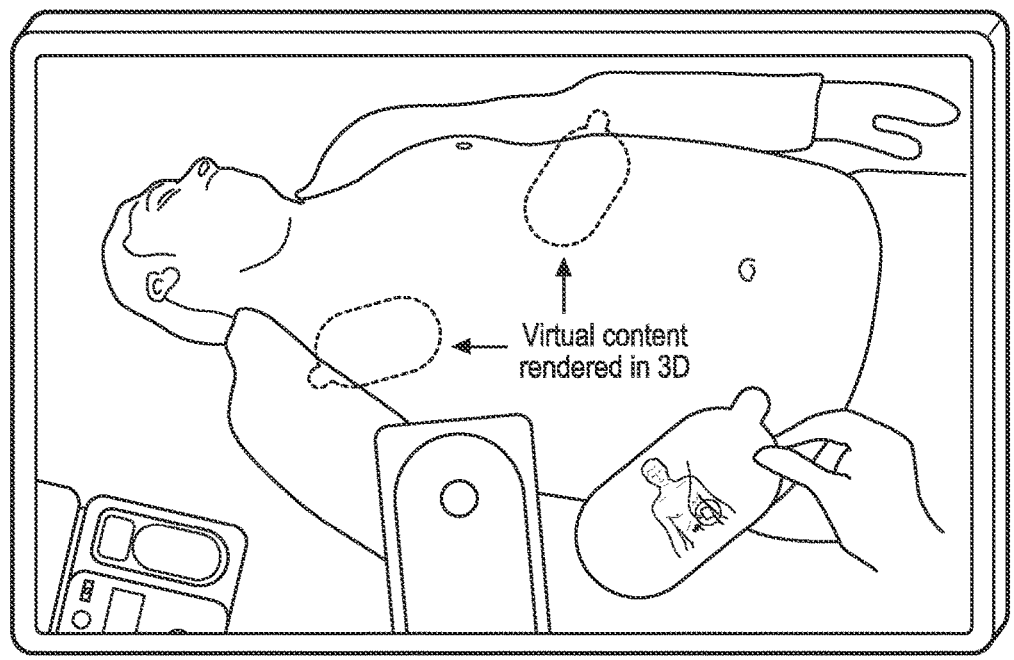
FIG. 5 is a combined image and corresponding annotation view as displayed in augmented reality glasses of a first responder using the portable device with a subject at a scene, showing placement of the 3D virtual content per the remote assistant inputs in the second pane of the graphical user interface of FIG. 4, according to an embodiment of the present disclosure.
Figure 5:
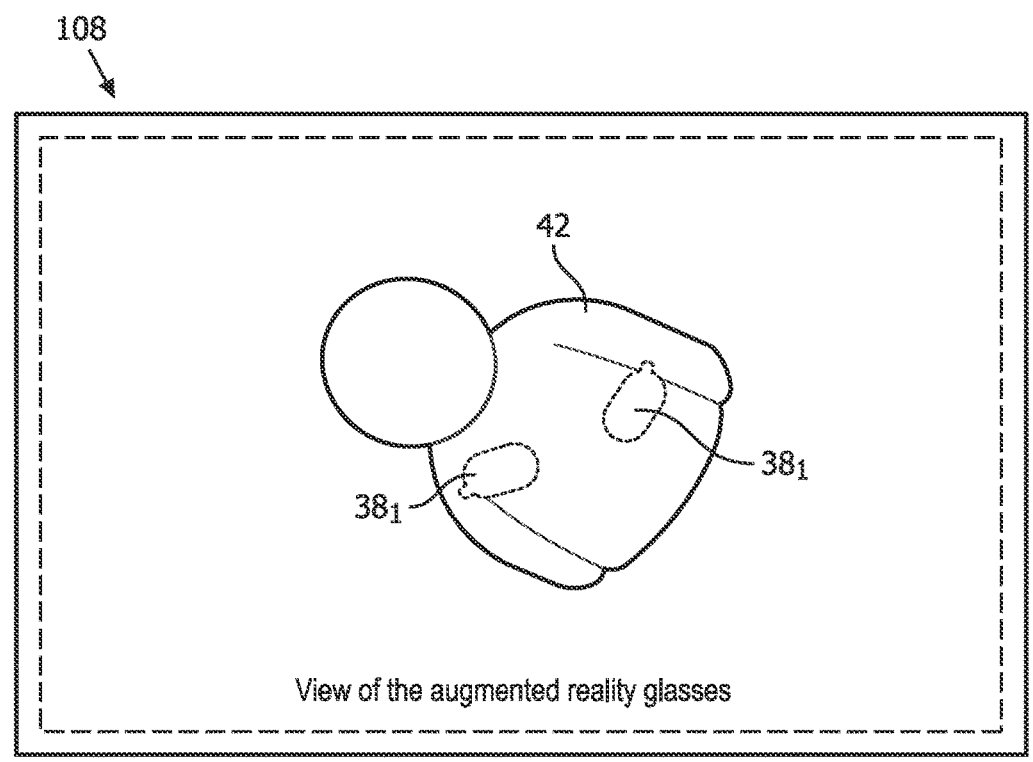

Turning now to FIG. 5, there is shown a combined image and corresponding annotation view as displayed in augmented reality glasses 36 of a first responder 34 using the portable device 14 with a subject 42 at the scene 40. The display 108 in the AR glasses 36 shows to the first responder 34 the remote assistant's placement of the 3D virtual content $38_1$ upon the live video view of the first pane 96 of the remote assistant graphical user interface 100, in response to the remote assistant inputs in the second pane 98 of the graphical user interface 100 of FIG. 4, according to an embodiment of the present disclosure. In other words, responsive to the remote expert selecting and moving virtual content in the 2D pane (i.e., the second pane), then the virtual content appears correctly in perspective in the AR glasses of the first responder. In the image view of FIG. 5, the first responder's hand can be seen holding one of the AED electrodes in preparation for placement of the same upon the victim's chest, using the remote assistant's placement of the 3D virtual content 38 upon the live video view for spatial placement guidance and/or assistance.

With reference now to FIG. 6, there is illustrated a combined image and corresponding annotation view of the first and second panes, indicated by reference numerals 96 and 112, respectively, of a remote assistance workstation graphical user interface 110. In this embodiment, the second pane 112 comprises one or more tabs 105, 107 and 109 available for selection by the remote assistant during a given remote assistance application, the tabs being similar or in addition to those discussed herein above with reference to tabs 99, 101 and 103 of FIG. 4. For example, responsive to selection of tab 105 in FIG. 6, the remote assistant is provided with information regarding the victim's identification and medical record information, similar to that of pane 106 of FIG. 4. In addition, the first pane 96 also includes a location information insert 104 as was discussed with reference to FIG. 4. Still further, the graphical user interface 110 can include another pane 114 which presents a map showing a geographical location of the victim, if available, from a suitable mapping source.

With reference still to FIG. 6, in the live video of the first pane 96, the remote assistant 32 points to a location within the live video to identify or highlight a desired location 116 within the live scene for the first responder 34. In particular, FIG. 6 shows a remote assistant input that comprises an (x,y) coordinate selection being received in the first pane 96 of the graphical user interface 110, according to an embodiment of the present disclosure. In one embodiment, the highlight comprises a circle outline, or it can also comprise any geometric shaped highlight suitable for a given remote assistance application.

Turning now to FIG. 7, there is shown a combined image and corresponding annotation view as displayed in augmented reality glasses 36 of the first responder 34 using the portable device 14 with a subject 42 at the scene 40. The display 118 in the AR glasses 36 shows placement of a highlight 116 at a corresponding (x,y) coordinate per the remote assistant input in the first pane 96 of the graphical user interface 110 of FIG. 6, according to an embodiment of the present disclosure. In other words, the remote assistant can touch an (x,y) coordinate (i.e., select the (x,y) coordinate) in the video pane (i.e., the first pane), causing a highlight to appear at the same (x,y) coordinate in the AR glasses of the first responder.

FIG. 8 is a flow diagram view of a method 150 for providing remote assistance with spatial placement tasks via a user interface of a remote assistance workstation and a portable device, according to an embodiment of the present disclosure. In a first step, a portable device is provided at a scene, wherein the portable device comprises at least a pair of stereoscopic augmented reality glasses for use by a first responder to carry out at least one action using a first object at the scene in connection with a subject or a second object at the scene (Step 152).

In a next step (Step 154), the method includes operatively coupling the remote assistance workstation to the portable device in response to a remote assistance request initiated from the portable device. For example, the first responder can request remote assistance via selecting one or more of a prescribed button or soft-key on the portable device, configured for sending a request for remote assistance to the remote assistance workstation. In one embodiment, the request for remote assistance includes providing live video as seen from a camera of the augmented reality glasses to the remote assistance workstation.

In a next step (Step 156), the method comprises rendering a remote assistant graphical user interface (GUI) on a display device of a remote assistance workstation, and receiving remote assistant inputs, the remote assistant GUI including a first pane for displaying a live video stream of the remote assistance request and a second pane for displaying a 2D representation of a first object at the scene.

In a next step (Step 158), the method comprises generating one or more remote assistance signals to be output to the portable device for displaying at least one item of 3D virtual content on the stereoscopic augmented reality glasses to the first responder within a live view in response to one or more remote assistant inputs selecting and moving a 2D representation of the first object at the scene within the second pane of the remote assistance GUI.

The embodiments of the present disclosure advantageously enable selecting and moving of 3D virtual content quickly and intuitively. For example, the remote assistant can select and move the virtual content in a 2D plane hovering above the victim (i.e., the virtual content in the second pane hovering above a top view 2D representation of the victim). From face recognition, the orientation of the victim's body may be derived and the 2D XY coordinate system of the screen (i.e., in the second pane) can be aligned with the XY coordinate system of the body (i.e., in the first pane) in which the Y axis is the body's midline, so that when the remote assistant moves a 2D representation of a 3D virtual object in the Y-direction on screen (i.e., in the second pane), the virtual object moves parallel to the victim's midline.

Under emergency circumstances, the first responder's perspective can change as the first responder provides emergency assistance to the victim. When the first responder moves his or her head (and he or she will because of the nature of the task), the instructor (remote expert/assistant) can select and move the 3D virtual content on the 2D screen (i.e., in the second pane) and this selected virtual content will be perspectively stable in the AR glasses of the first responder. In other words, responsive to 3D virtual content being selected and positioned within the 2D screen, the perceptual positioning of the 3D virtual content is not disturbed by movements of either the first responder or the remote expert/assistant (unless of course, the remote expert/assistant pro-actively, purposefully or affirmatively selects and moves the 2D representation of the 3D virtual content).

Although only a few exemplary embodiments have been described in detail above, those skilled in the art will readily appreciate that many modifications are possible in the exemplary embodiments without materially departing from the novel teachings and advantages of the embodiments of the present disclosure. For example, while the embodiments of the present disclosure have been described herein in the context of emergency care, the embodiments are equally applicable to other use cases involving remote assistance using augmented reality (AR). Accordingly, all such modifications are intended to be included within the scope of the embodiments of the present disclosure as defined in the following claims. In the claims, means-plus-function clauses are intended to cover the structures described herein as performing the recited function and not only structural equivalents, but also equivalent structures.

In addition, any reference signs placed in parentheses in one or more claims shall not be construed as limiting the claims. The word "comprising" and "comprises," and the like, does not exclude the presence of elements or steps other than those listed in any claim or the specification as a whole. The singular reference of an element does not exclude the plural references of such elements and vice-versa. One or more of the embodiments may be implemented by means of hardware comprising several distinct elements, and/or by means of a suitably programmed computer. In a device claim enumerating several means, several of these means may be embodied by one and the same item of hardware. The mere fact that certain measures are recited in mutually different dependent claims does not indicate that a combination of these measures cannot be used to an advantage.

The invention claimed is:

1. A remote assistance workstation configured for being operatively coupled to a portable device that comprises at least a pair of stereoscopic augmented reality glasses, the portable device for use by a first responder to carry out at least one action using a first object at a scene in connection with at least one of (i) a subject; and (ii) second object at the scene, the remote assistance workstation comprising:

a communications module, configured for communicating with the portable device in response to a remote assistance request initiated from the portable device; the remote assistance request including at least a live video stream captured via a camera of the stereoscopic augmented reality glasses at the scene;

a user interface module configured for (a) rendering a remote assistant graphical user interface on a display device and (b) receiving remote assistant inputs from a remote assistant, wherein the remote assistant graphical user interface includes at least (i) a first pane that comprises a 3D pane for displaying the live video stream of the remote assistance request, and (ii) a second pane that comprises a 2D pane for displaying a 2D representation of the first object at the scene, wherein the rendered 2D representation is moveable within the second pane in response to one or more remote assistant inputs, the remote assistant graphical user interface further for rendering within the first pane an item of 3D virtual content that corresponds with the rendered 2D representation of the first object at the scene within the second pane, relative to at least a reference point within the first pane, wherein the reference point is based upon a content of the live video stream; and a controller for generating one or more remote assistance signals to be output, via the communications module, to the portable device for displaying, in response to the one or more remote assistant inputs moving the rendered 2D representation of the first object at the scene within the second pane, the item of 3D virtual content on the stereoscopic augmented reality glasses to the first responder within a live view of the scene as is captured by the camera of the stereoscopic augmented reality glasses, such that the item of 3D virtual content appears at a correct location with respect to the reference point within the live view, for assisting the first responder to carry out the at least one action using the first object in connection with the subject or the second object at the scene.

2. The remote assistance workstation according to claim 1, wherein the portable device comprises a portable medical device that includes at least one of an automated external defibrillator (AED), a cardiopulmonary resuscitation (CPR) metronome, and an electrocardiogram (ECG) monitor, and wherein the first object at the scene comprises one or more of (i) a first responder's hand, hands, or other first responder body part, and (ii) at least one item of the portable device.

3. The remote assistance workstation according to claim 2, further wherein the item of 3D virtual content comprises a virtual representation outline that is representative of at least one of (i) the first responder's hand, hands, or other first responder body part, and (ii) the at least one item of the portable device.

4. The remote assistance workstation according to claim 1, further comprising one or more of:

a video rendering module, wherein the video rendering module is operable for rendering at least the live video stream of the remote assistance request within the first pane;

a 2D graphical view rendering module, wherein the 2D graphical view rendering module is operable for rendering within the second pane at least (i) a 2D representation of the subject or the second object at the scene, and (ii) the 2D representation of the first object at the scene;

a reference point module, wherein the reference point module is operable for establishing the reference point within the content of the live video stream of the remote assistance request and displayed in the first pane; and an XY coordinate module, wherein the XY coordinate module is operable for establishing an XY coordinate system in the first pane based at least upon the reference point for the live video stream of the remote assistance request.

5. The remote assistance workstation according to claim 4, wherein the reference point comprises at least one of (i) the subject's face determined via a face recognition algorithm applied to an image of the subject in the live video stream and (ii) a remote assistant selected reference point within the content of the live video stream rendered in the first pane.

6. The remote assistance workstation according to claim 5, further wherein the remote assistant selected reference point comprises at least one of (i) a reference point on the subject or second object at the scene, (ii) a reference point on the portable device, and (iii) a reference point on the first object.

7. The remote assistance workstation according to claim 6, wherein the remote assistant selected reference point further comprises a vertical direction, wherein the vertical direction is selected by modifying a view of the second pane by rotating the view so that the vertical direction of the view corresponds with a central axis of the subject or the second object at the scene.

8. The remote assistance workstation according to claim 4, wherein the one or more remote assistance signals are further configured for displaying at least one highlight on the stereoscopic augmented reality glasses to the first responder within the live view of the scene captured by the camera, in response to at least one remote assistant input that comprises the remote assistant selecting an XY coordinate in the live video stream displayed in the first pane of the remote expert graphical user interface, further wherein the at least one highlight is displayed at a matching XY coordinate in the augmented reality glasses as seen by the first responder.

9. The remote assistance workstation according to claim 4, further wherein the second pane includes at least one tab for each of a plurality of types of actions to be carried out in connection with the subject or second object at the scene, wherein responsive to a remote assistant selecting, via the remote assistant graphical user interface, a given tab in the second pane, the 2D graphical view rendering module renders within the second pane tone or more 2D representation of the first object associated with the given tab available for use by the remote assistant with respect to a corresponding given type of action.

10. The remote assistance workstation according to claim 9, wherein the portable device comprises a portable medical device that includes at least one of an automated external defibrillator (AED), a cardiopulmonary resuscitation (CPR) metronome, and an electrocardiogram (ECG) monitor, further wherein the one or more 2D representation of the first object correspond with one or more of (i) a first responder's hand, hands, or other first responder body part, and (ii) at least one item of the portable device.

11. The remote assistance workstation according to claim 10, wherein one or more 2D representation of the at least one item of the portable device is further representative of at least one selected from the group consisting of: AED pad placement, CPR compression placement, and ECG sensor placement.

12. The remote assistance workstation according to claim 1, further comprising the display device, wherein the display device includes a touch screen device for receiving the remote assistance inputs.

13. A method for providing remote assistance via a remote assistance workstation and a portable device, wherein the portable device comprises at least a pair of stereoscopic augmented reality glasses, the portable device for use by a first responder to carry out at least one action using a first object at a scene in connection with at least one of (i) a subject and (ii) a second object at the scene, the method comprising:

operatively coupling, via a communications module, the remote assistance workstation to the portable device, in response to a remote assistance request initiated from the portable device; the remote assistance request including at least a live video stream captured via a camera of the stereoscopic augmented reality glasses at the scene;

rendering, via a user interface module, a remote assistant graphical user interface on a display device and receiving remote assistant inputs from a remote assistant, wherein the remote assistant graphical user interface includes at least (i) a first pane that comprises a 3D pane for displaying the live video stream of the remote assistance request, and
(ii) a second pane that comprises a 2D pane for displaying a 2D representation of the first object at the scene, wherein the rendered 2D representation is moveable within the second pane in response to one or more remote assistant inputs, wherein remote assistant graphical user interface further renders within the first pane an item of 3D virtual content that corresponds with the rendered 2D representation of the first object at the scene within the second pane, relative to at least a reference point within the first pane, wherein the reference point is based upon a content of the live video stream; and generating, via a controller, one or more remote assistance signals to be output, via the communications module, to the portable device for displaying, in response to the one or more remote assistant inputs moving the rendered 2D representation of the first object at the scene within the second pane, the item of 3D virtual content on the stereoscopic augmented reality glasses to the first responder within a live view of the scene as is captured by the camera of the stereoscopic augmented reality glasses, such that the item of 3D virtual content appears at a correct location with respect to the reference point within the live view for assisting the first responder to carry out the at least one action in connection with the subject or the second object at the scene.

14. The method according to claim 13, wherein the portable device comprises a portable medical device that includes at least one of an automated external defibrillator (AED), a cardiopulmonary resuscitation (CPR) metronome, and an electrocardiogram (ECG) monitor, and wherein the first object at the scene comprises one or more of (i) a first responder's hand, hands, or other first responder body part, and (ii) at least one item of the portable device.

15. The method according to claim 14, further wherein the item of 3D virtual content comprises a virtual representation outline that is representative of at least one of (i) the first responder's hand, hands, or other first responder body part, and (ii) the at least one item of the portable device.

16. The method according to claim 13, wherein generating, via the controller, further comprises generating one or more remote assistance signals for displaying at least one highlight on the stereoscopic augmented reality glasses to the first responder within the live view of the scene captured by the camera, in response to at least one remote assistant input that comprises the remote assistant selecting an XY coordinate in the live video stream displayed in the first pane of the remote expert graphical user interface, further wherein the at least one highlight is displayed at a matching XY coordinate in the augmented reality glasses as seen by the first responder.

17. The method according to claim 13, wherein the reference point comprises one selected from the group consisting of
(i) a reference point of the subject's face determined via a face recognition algorithm applied to an image of the subject in the live video stream rendered in the first pane, and
(ii) a remote assistant selected reference point within the content of the live video stream rendered in the first pane.

18. The method according to claim 17, further wherein the remote assistant selected reference point comprises at least one of (i) a reference point on the subject or second object at the scene, (ii) a reference point on the portable device, and (iii) a reference point on the first object, and wherein selecting the remote assistant reference point further comprises modifying a view of the second pane by rotating the view so that a vertical direction of the view corresponds with a central axis of the subject or the second object at the scene.

19. A non-transitory computer-readable medium embodied with instructions that, when executed by a processor, cause the processor to carry out the method of claim 13.

20. A remote assistance system comprising:
a remote assistance workstation according to claim 1; and
a portable device, wherein the portable device comprises at least a pair of stereoscopic augmented reality glasses and the first object at the scene comprises one or more of (i) a first responder's hand, hands, or other first responder body part, and (ii) at least one item, further wherein the portable device is for use by a first responder to carry out at least one action in connection with at least one of a subject and a second object at a scene, wherein the portable device further comprises a communications module configured for communicating with the remote assistance workstation, wherein the at least one item comprises at least one workpiece for use by the first responder in connection with carrying out the at least one action on the subject or second object at the scene, and wherein the at least a pair of stereoscopic augmented reality glasses to be worn by the first responder includes a camera for capturing real-time images of the subject or second object at the scene.

* * * * *